United States Patent [19]
Moreau Defarges et al.

[11] Patent Number: 6,053,890
[45] Date of Patent: Apr. 25, 2000

[54] NEEDLELESS JET INJECTION DEVICE COMPRISING A MOULDED-ON CARTRIDGE

[76] Inventors: Alain Moreau Defarges, 2, avenue Léopold-II, 75016, Paris; Xavier Moreau Defarges, 80 Rue de la Liberté, 92150 Suresnes, both of France

[21] Appl. No.: 09/051,290
[22] PCT Filed: Oct. 9, 1996
[86] PCT No.: PCT/FR96/01573
§ 371 Date: Aug. 31, 1998
§ 102(e) Date: Aug. 31, 1998
[87] PCT Pub. No.: WO97/13536
PCT Pub. Date: Apr. 17, 1997

[30] Foreign Application Priority Data

Oct. 9, 1995 [FR] France ................................. 95 11872

[51] Int. Cl.⁷ ................................................. A61M 5/30
[52] U.S. Cl. ........................... 604/68; 604/232; 604/403
[58] Field of Search ................................. 604/68, 70–73, 604/131, 134, 403, 232–234

[56] References Cited

U.S. PATENT DOCUMENTS

| | | | |
|---|---|---|---|
| 2,687,730 | 8/1954 | Hein, Jr. ..................................... | 604/72 |
| 2,737,946 | 3/1956 | Hein, Jr. ..................................... | 604/70 |
| 2,813,528 | 11/1957 | Blackman . | |
| 3,130,724 | 4/1964 | Higgins et al. . | |
| 3,688,765 | 9/1972 | Gasaway .................................... | 604/70 |
| 3,848,593 | 11/1974 | Baldwin .................................... | 604/206 |
| 3,895,633 | 7/1975 | Bartner et al. . | |
| 4,333,456 | 6/1982 | Webb ........................................ | 604/206 |
| 4,664,655 | 5/1987 | Orentreich et al. ...................... | 604/232 |
| 4,722,728 | 2/1988 | Dixon ........................................ | 604/68 |
| 4,830,217 | 5/1989 | Dufresne et al. . | |
| 4,915,701 | 4/1990 | Halkyard .................................. | 604/198 |
| 4,982,769 | 1/1991 | Fournier et al. . | |
| 5,064,413 | 11/1991 | Mckinnon et al. ....................... | 604/70 |
| 5,256,142 | 10/1993 | Colavecchio ............................. | 604/68 |
| 5,332,399 | 7/1994 | Grabenkort et al. .................... | 604/415 |
| 5,334,144 | 8/1994 | Alchas et al. ............................ | 604/68 |
| 5,350,367 | 9/1994 | Stiehl et al. ............................. | 604/232 |
| 5,514,107 | 5/1996 | Haber et al. ............................. | 604/197 |
| 5,569,236 | 10/1996 | Kriesel . | |
| 5,730,723 | 3/1998 | Castelano et al. ....................... | 604/68 |
| 5,989,227 | 11/1999 | Vetter et al. ............................. | 604/232 |

FOREIGN PATENT DOCUMENTS 677523  8/1952  United Kingdom .

Primary Examiner—Wynn Wood Coggins
Assistant Examiner—LoAn H. Thanh
Attorney, Agent, or Firm—Pollock, Vande Sande & Amernick

[57] ABSTRACT

A needleless jet injection device including a barrel fitted with a cap at one of the ends thereof. Relative motion of the cap component actuates a setting device operably connected to a precussive member. A cartridge arranged at the other end of the barrel comprises two elements, i.e., a first element forming a container for the active principle, and a second element consisting of a plastic shell enclosing the first element.

5 Claims, 4 Drawing Sheets

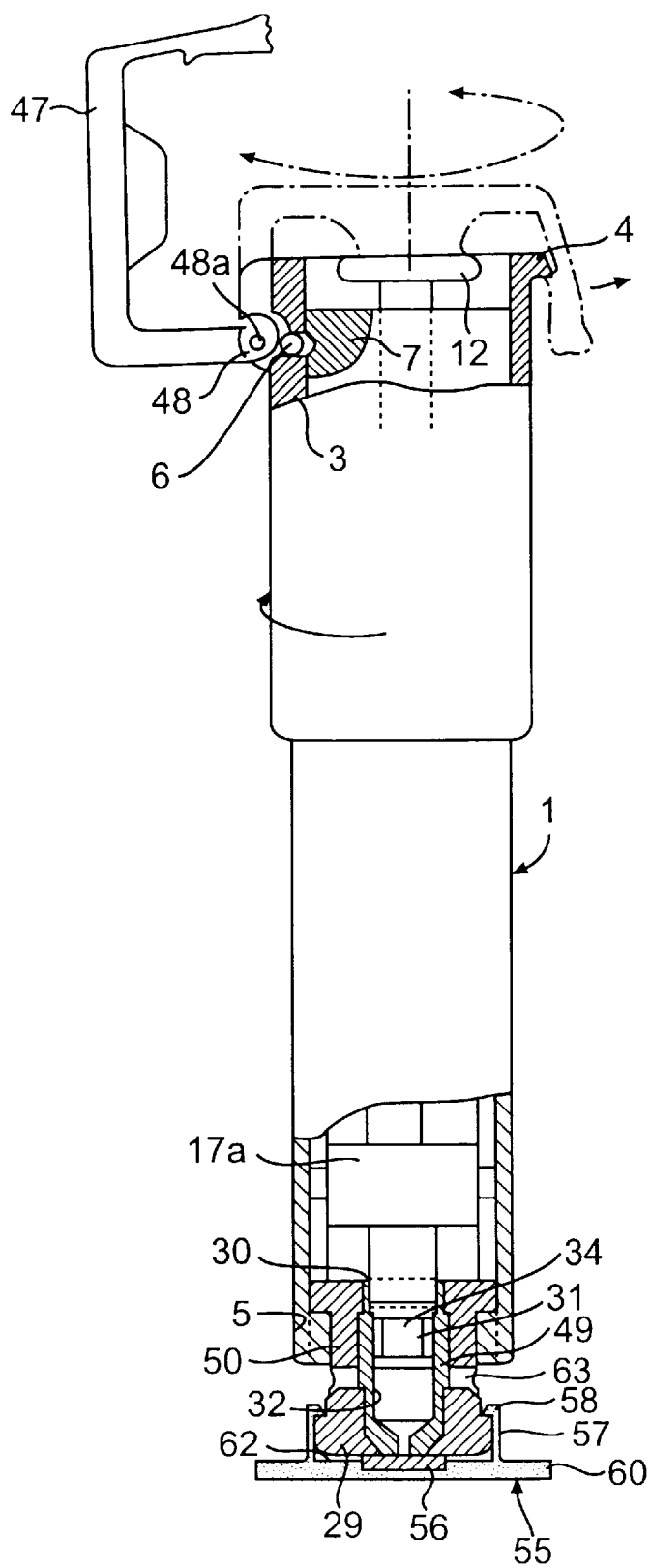
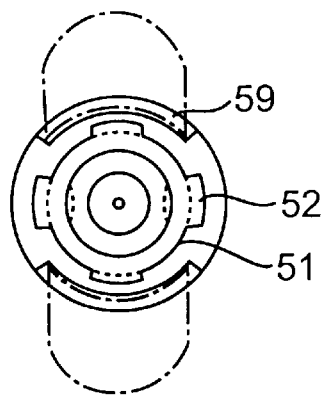
FIG. 10
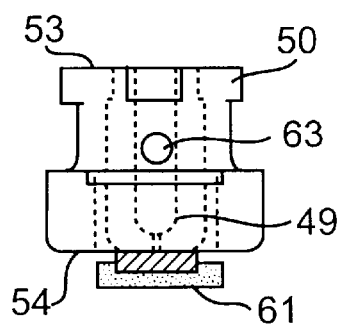
FIG. 11
FIG. 9

NEEDLELESS JET INJECTION DEVICE COMPRISING A MOULDED-ON CARTRIDGE

FIELD OF THE INVENTION

The present invention relates to a device permitting the injection of a product, in particular a pharmaceutical product, into the human or animal body.

It concerns more particularly an apparatus without hypodermic needle, equipped with an arming system, which permits the subcutaneous, intradermal or intramuscular administration of medical substances or vaccines, contained in a single dose, and forming a cartridge.

BRIEF DESCRIPTION OF THE PRIOR ART

Apparatuses for injection by transcutaneous jet without needle are known which have been developed for veterinary or human medicine. The absence of a needle simplifies the use of the apparatus and does not require specific knowledge on the part of the user. They are generally used for mass vaccination campaigns and are designed to be used quickly by nonspecialist personnel. The use of a jet avoids to the greatest extent bacterial and/or viral contamination of one subject by another, which happens in those cases where the same needle is used by several subjects without being sterilized. These apparatuses are generally designed in a pistol shape, equipped with a receptacle for the product which is to be injected, driven through a nozzle, by the action of a plunger displaced within a chamber, filled beforehand with the substance, the plunger being moved by a striker. Alternatively the pistol includes a breech or a magazine containing a cartridge, also placed in the axis of the striker.

Thus, the document WO 95/03844 discloses a device for injection by jet without needle, which is provided with an arming device activated by the rotation of a cap situated at one of the ends of the body of the device.

The document WO 95/27523 describes a device for injection by jet without needle, provided at one of its ends with a cartridge formed in one piece.

The document WO 96/15821 describes a cartridge including a capsule on which a sleeve tube is fitted by force and induces stresses on the capsule.

Finally, the document EP 427 457 describes a device for injection by jet without needle, provided with a cartridge which cooperates at one of the ends of the device, by way of a component forming a breech.

Given the mode of action of the striker, which has a substantial kinetic energy before reaching the plunger of the cartridge, which can, in cases where the cartridge is not correctly arranged in the magazine of the pistol, cause it to burst at the start of the injection, these apparatuses are not reliable and are not easy to use if their use is infrequent.

The present invention is therefore aimed at overcoming these disadvantages by making available a device which is without magazine for a cartridge and which permits the injection by jet, without needle, of the product contained in a cartridge placed directly at the head of the device, under strictly aseptic conditions, for a single use.

For this purpose, the cartridge for injection of a product, in particular a pharmaceutical product, by jet without needle, for single use, and intended to be fixed at a first end of the body of an injection device, the second end of the body receiving a cap which is able, by virtue of a relative movement of the body, to drive an arming device, cooperating with a percussion member intended to cooperate with the cartridge, is characterized in that it includes two elements:

the first element made of glass forms the receptacle intended to contain the product;

the second element consists of an envelope of plastic material which is overmoulded on the first element.

Other characteristics and advantages of the present invention will be evident from the description which follows, with reference being made to the attached drawings which show an illustrative embodiment of the invention, without this embodiment in any way being of a limiting character. In the figures:

BRIEF DESCRIPTION OF THE DRAWINGS

FIG. 9 is a plan view, in front elevation and in section, of the device according to the invention;

FIG. 10 is a plan view, in front elevation and in section, of a cartridge according to a second embodiment;

FIG. 11 is a plan view, in side elevation and in section, of a cartridge according to a second embodiment.

DETAILED DESCRIPTION

Figure 1:
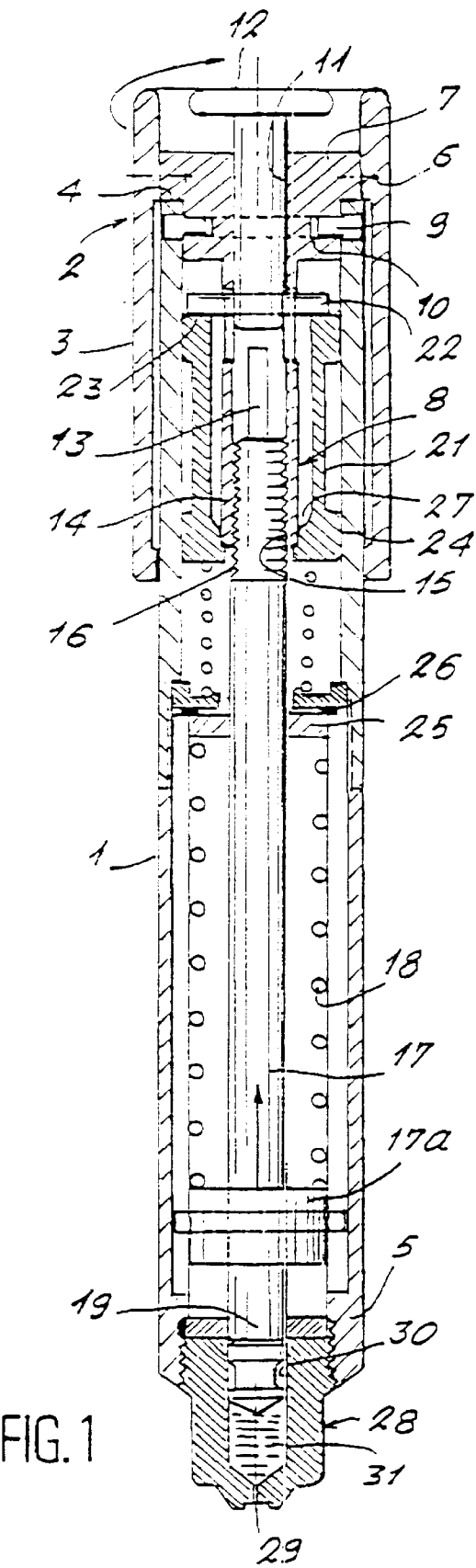
FIG. 1 is a plan view, in front elevation and in section, of the device according to the invention, in the armed position.
Figure 2:
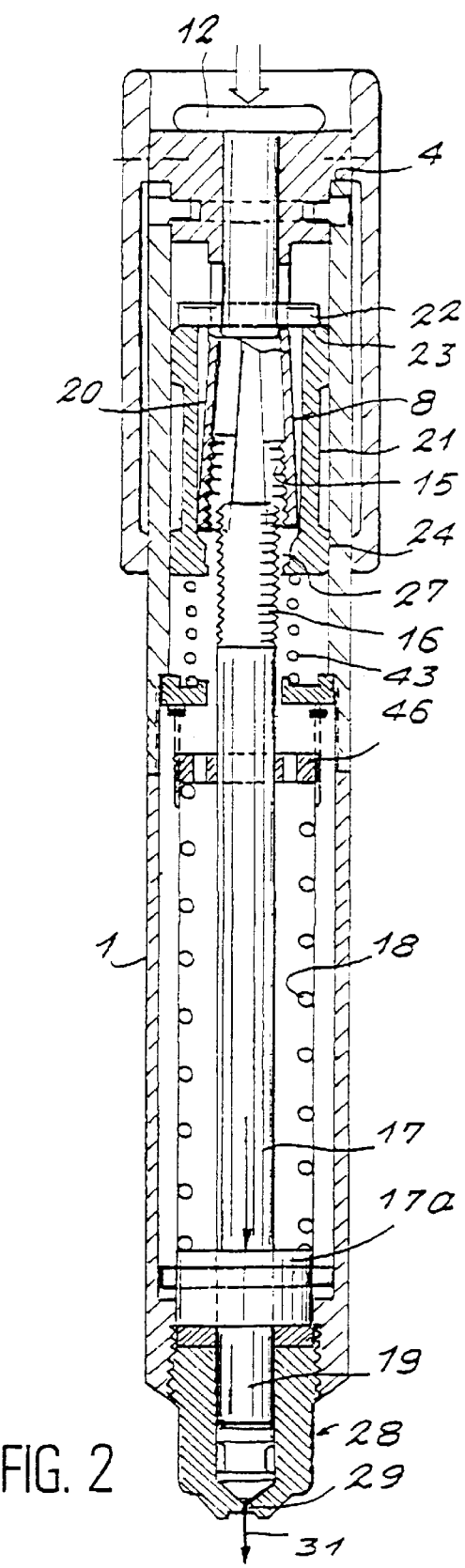
FIG. 2 is a plan view, in front elevation and in section, of the device according to the invention, in the triggered position.
Figure 6:
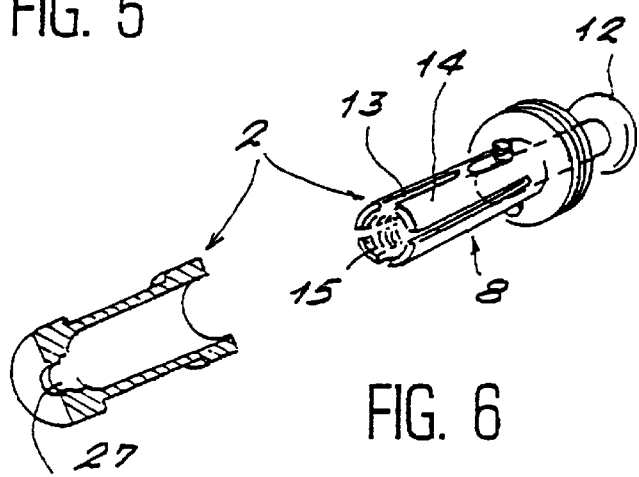
FIG. 6 is a perspective view of the clamp system intended to hold the rod of the striker.
Figure 8:
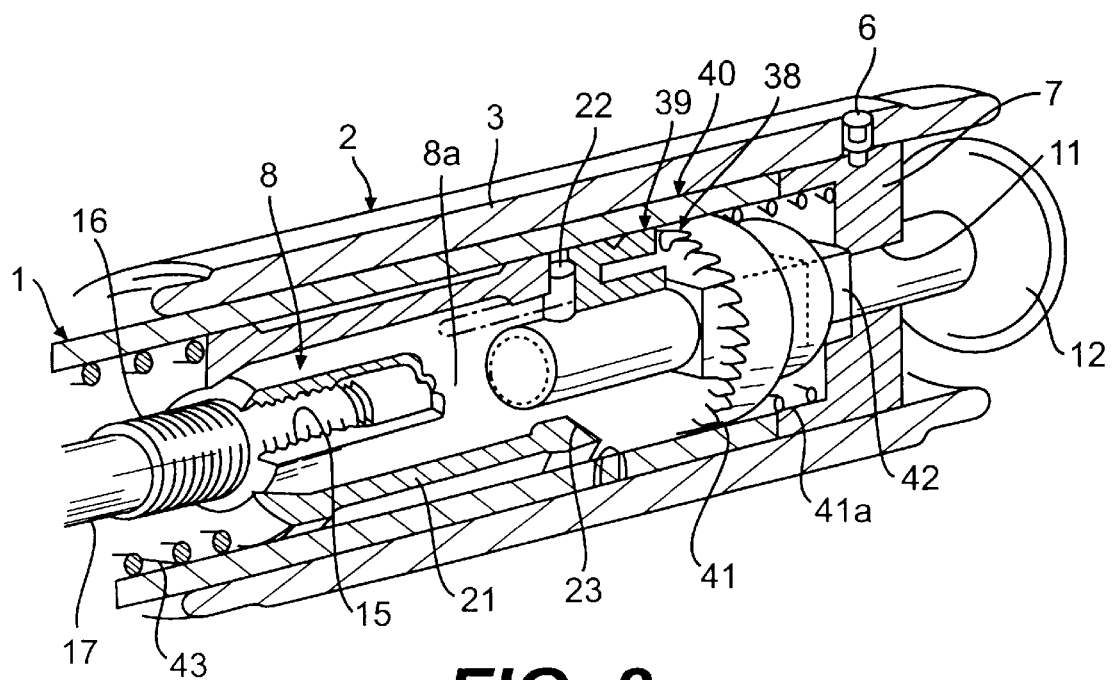
FIG. 8 is a perspective view of the releasable connection member.

According to a preferred embodiment, the device which is the subject of the invention essentially comprises a body 1 extending in the form of a tube, in particular of straight cylindrical cross-section, intended to receive an arming device 2 connected to a cap 3, in particular knurled in order to improve its grip by the user, provided at one of the ends 4, 5 of the body. Viewing FIG. 8, the cap is made from a tube portion, of similar cross-section to that of the main body of the said device, the diameter of which, however, is greater in order to permit a relative rotational movement thereof about the body, and it cooperates by way of a catch device 6, in particular of the key type, with a ring 7, itself integral with a clamp 8. The ring is engaged with play at the end of the body 1 and can turn freely in the body, its axial position in the tube being determined by a radial abutment 9 on the wall of the tube and fitting in a circular groove 10 formed on the said ring 7 and positioned opposite the abutment 9. The rotational movement from the cap 3 is transmitted to the ring by way of the catch device 6. The ring 7 is additionally provided with a central recess 11 for the passage of a striker 12, free in axial translation and leading inside the clamp 8. This clamp constitutes one of the links of the arming device. Of overall cylindrical shape, it is equipped with a plurality of cutouts 13 oriented substantially parallel to the axis of the body in such a way as to form a plurality of flexible tabs 14 (FIG. 6). In addition, the inner bore 15 (FIG. 8) of the clamp 8 is tapped in such a way as to form impressions which can be screwed around a threaded portion 16 provided on a rod 17 of the percussion striker 12. The thread pitch is determined as a function of the chosen demultiplication and the stiffness constant of a spring 18. The power of the striker can also be adjusted by means of pre-setting the compression of the spring, it being possible for the space between the turns to be set by way of a knurled wheel 46 (as shown in FIG. 1) displaced on the rod 17 and in contact with 18 or alternatively by way of a stack of washers arranged between the spring 18 and a ring 25 as shown in FIG. 2. The turns of the spring 18 are compressed by the relative rotational movement between the cap 3 and the body 1.

According to an advantageous characteristic of the invention, the cap 3 includes a safety device 47 (FIG. 9) which covers the rod of the striker 12. This safety device 47 is connected to the cap 3 by way of a hinge 48 which permits a rotational movement of the safety device 47, between a horizontal locked position shown in dotted lines and an unlocked vertical position shown in solid lines of the rod of the striker 12. The rotation of the safety device 47 to the horizontal position also makes it possible to act on the catch member 6 between the cap 3 and the ring 7. This is because it is essential that the user can arm the percussion device (striker 12 and rod 17) only when the safety device 47 is covering the rod of the striker 12 (horizontal position); this is why, when the safety device 47 is locked (horizontal position) on the cap 3, it acts on the catch member 6 in such a way that the latter permits the transmission of the rotational movement between the cap 3 and the ring 7. In greater detail, the hinge 48 of the safety device 47 is pivoted in an offset manner so as to create a camming surface against catch member 6 which is basically a detent member. Once the safety device 47 has been rotated to the armed position (indicated in phantom lines), hinge 48 cams the catch member 6 into the corresponding detent recess formed in ring 7, the catch member 6 effectively connecting the cap 3 and the ring 7 so as to allow mutual rotation and subsequent triggering.

When the safety device 47 is unlocked (vertical position), that is to say when it is no longer covering the rod of the striker 12, it no longer acts on the catch member 6 and the user cannot arm the percussion device.

There is therefore a rod 17, forming a plunger, arranged inside the said body 1, its length being chosen in such a way that its end 19, not connected to the clamp 8, extends toward the end 5 of the body 1 when the arming device 2 is operational. The lower end of rod 17 is guided by annular guide 17a.

The peripheral envelope 20 of the clamp is held by a spacer sleeve 21, also of a cross-section similar to that of the body, the external diameter of which corresponds to the internal diameter of the body in such a way as to form guide zones. Its axial position inside the body being limited, on the one hand, at one of its ends 23, 24, by a pin 22 passing radially right through the striker 12, and, on the other hand, its other front end constituting a bearing surface for a spring 43; the axial position of the spring and its other bearing surface being additionally limited, for example, by a ring 25 inserted in the body, integral with the rod 17 and axially immobilized, if appropriate, by a clip ring 26, or by a shoulder formed on the rod.

In the arming position, the user imparts a relative rotational movement between the body 1 and the cap 3; as we have seen above, the rotational movement of the cap is transmitted both to the said ring 7 and to the clamp 8 integral with the latter; the several threads of the clamp 8 in engagement with those of the rod make it possible to initiate the movement of translation between the rod 17 (forming the screw) and the clamp 8 (forming the nut) and the relative closing-together of these two components. This translation movement compresses the turns of the spring 18 until the space between the turns is reduced to the maximum. According to another embodiment, the spiral spring can be replaced by a helical spring or by any other elastic device.

In the disarm or trigger position, the user exerts a slight push on the striker 12, the pin 22, projecting radially and in contact with one of the front faces 23, 24 of the spacer sleeve, transmits a relative movement (through slot 8a, FIG. 8) of translation between the spacer sleeve 21 and the clamp 8, which releases the end thereof from a conical bearing surface 27 provided at the bottom of the bore of the spacer sleeve 21. The thrust of the spring 18 combined with the flexibility of the tabs of the clamp frees the respective threads previously in engagement, thereby provoking an almost impulse movement of translation of the whole rod.

Figure 7:
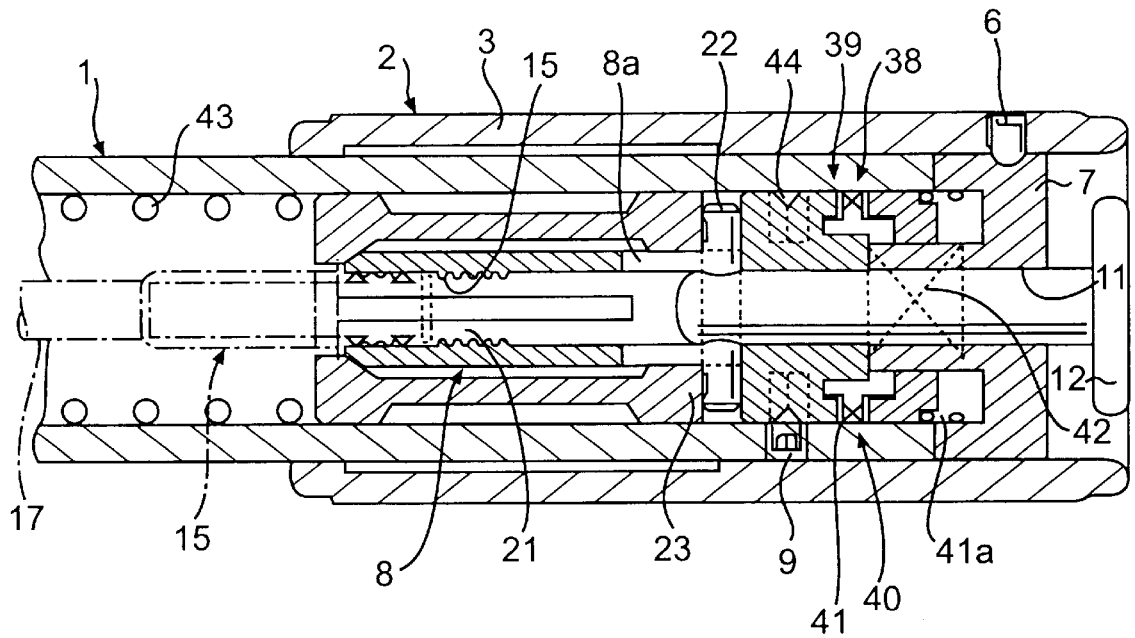
FIG. 7 is a plan view, in front elevation and in section, of the device according to another embodiment of the invention, including a releasable connection member.

According to another embodiment of the invention (FIGS. 7 and 8), there is arranged, between the cap 3 and the arming member integral with the clamp 8 contained in the body 1, a connection member 38 which permits the relative rotational movement between these two components only in one direction of rotation. The reason is that, to avoid any damage to the apparatus and to simplify its handling by the user, a releasable connection member 38 is provided which is composed principally of two components 39, 40, in particular of circular cross-section. One of the components 39 is integral with the cap 3, while the other 40 is connected to the clamp 8 and to the body 1 by way of a groove 44, and each of the components also has, at their contact face, a plurality of raised zones (ratchet connection) 41. These zones 41 have a profile which is able, on the one hand, to permit a relative sliding between the components 39 and 40 in one direction of rotation between the cap 3 and the body 1 and, on the other hand, to transmit the moment in the other direction of rotation of the cap 3 relative to the body 1.

The raised zones 41 are preferably formed from a plurality of teeth, in particular of triangular cross-section.

For the connection member 38 to function, however, it is best not to suppress completely the movements of the components 39 and 40 in relation to the cap 3 and to the clamp 8; thus, when the connection member is active (released), it is necessary for the components 39, 40 to escape longitudinally from one another and for these components to return to their engaged position after suppression of the moment; for this reason, an elastic member 41a, in particular of the spring type, is arranged in line with the outer surface of one of the components 39 or 40, in the area of a guide portion 42, which compensates for the translation movements between the components.

According to another characteristic of the invention (FIGS. 9, 11), a cartridge 28 is arranged at the other end 5 of the body 1 of the device, by known means such as, in particular, being screwed on, clipped on (bushing, bayonet).

According to an advantageous characteristic of the invention, the cartridge 28 includes two elements 49, 50:

- the first element 49 forms the receptacle intended to contain the active principle, and it is obtained in particular from a type I medical-grade glass, since the receptacle is to contain injectable products;
- the second element 50 consists of an envelope of plastic material which covers the said first element 49.

The plastic material used in the overmoulding, that is to say covering, operation must be able to withstand a sterilization operation at high temperature (in the region of 120° C.), must be approved for pharmaceutical applications, must be insensitive to the temperature deviations in terms of its expansion, given that the cartridges 28 are generally stored in an atmosphere where the temperature is between 2 and 10° C. Moreover, after overmoulding on the first element 49, the plastic material employed is translucent, even transparent, and can be tinted. The product called _TPX_ (polymethylpentene) will be chosen, for example, as the plastic material.

The first element 49 made of glass, and overall of substantially cylindrical shape, includes, at each end, an orifice 29, 30. One 30 of the orifices has a diameter substantially equivalent to the diameter of the rod 17, while the other 29, of small diameter, in particular of the order of a few tenths of a millimeter, serves as nozzle. The internal cavity of the said cartridge is filled under vacuum with an active principle 31 and is, if appropriate, covered with a film 32 of material compatible with the physicochemical properties of the said product, in order to limit to the maximum the phenomenon of adsorption.

The cartridge 28, thus formed by the overmoulding of a plastic material on a first element 49 made of glass, includes, at one of its ends, means 51 (FIG. 10) permitting the engagement and fixing of the cartridge on the nose of the injection device.

The means 51 permitting the engagement and fixing are advantageously formed during the overmoulding operation by way of a plurality of studs 52 which project radially and are arranged along the diameter of the cartridge 28, these studs cooperating with the bayonets provided at the end 53 of the injection device.

The other end 54 of the cartridge 28 is designed as a plane surface intended to be applied against the surface of the skin of the user.

The outlet orifice 29 formed on this end 54 must be protected from possible contamination by the surrounding environment, and for this purpose there is an end cap 55 which is provided at its center with an elastomeric seal 56, in particular of silicone.

According to another embodiment, a film covering the surface of the cartridge 28 is arranged on the end 54.

This cap 55 is obtained by a process of moulding of plastic material, if appropriate, similar to that forming the cartridge.

The end cap 55 advantageously has lateral walls 57 which enclose the end of the cartridge 28, the said walls 57 being provided, at their ends, with raised zones 58 allowing them to be clipped into impressions 59 provided on the outer lateral walls of the cartridge 28, thus ensuring that the end cap 55 is held on the cartridge.

The upper wall 60 of the end cap 55 forms a grip zone which allows the user to position the studs 52 of the cartridge 28 in line with the bayonets of the injection device and, by a simple movement of rotation, to block the studs 52 in the bayonets and, after blocking the studs 52, when the user continues to impart this rotational movement to the end cap 55 and thus to the cartridge 28 which is integral with it, to detach the lateral walls 57 of the end cap 55 from the impressions 59 in the cartridge 28, in such a way as to make the injection device ready for use.

According to a first alternative, the elastomeric seal 56 is obtained during a simultaenous operation of moulding of the end cap 55.

According to a second alternative, the elastomeric seal 56 is attached and fitted by force into a recess 61 provided on the internal wall 62 of the end cap 55.

According to another advantageous characteristic of the invention, it is intended to form a plurality of plastic material gaps in the thickness of the plastic overmould of the cartridge 28, in order to produce slots 63 for improving the visibility of the first element 49 made of glass. The cartridge 28 thus obtained is for single use and is therefore disposable.

After filling, the orifice 30 of the cartridge (FIG. 5) is closed off by a protective cover 33 in order to guarantee satisfactory aseptic conditions. It is also intended to interpose, between the dose of product contained in the cavity of the cartridge and the protective sealing cover, an elastomeric stopper 34 for enclosing the dose, this stopper 34 being intended to communicate to the liquid the pressure exerted by the plunger of a striker.

According to an advantageous characteristic of the invention, the plunger of the striker is driven a few millimeters into the body of the cartridge so that the percussion force is directed and centered in the axis of the elastomeric stopper 34, in order to prevent any risk of bursting of the first glass element forming the cartridge 28.

Figure 3:
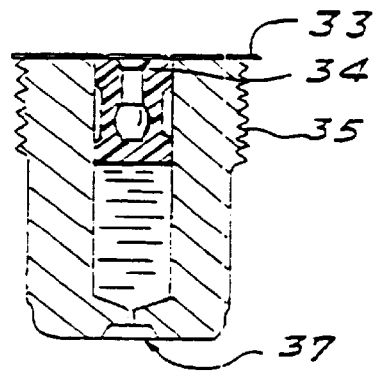
FIG. 3 is a view, on a larger scale and in section, of a cartridge containing a dose of injectable product.
Figure 4:
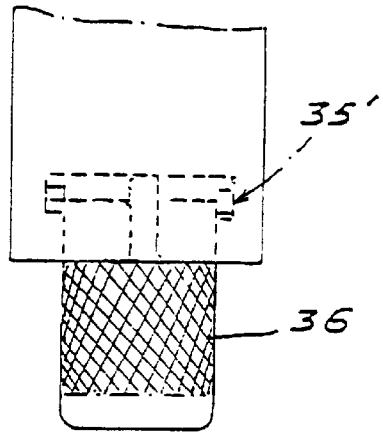
FIG. 4 is a view illustrating another method of fixing the cartridge on the device.
Figure 5:
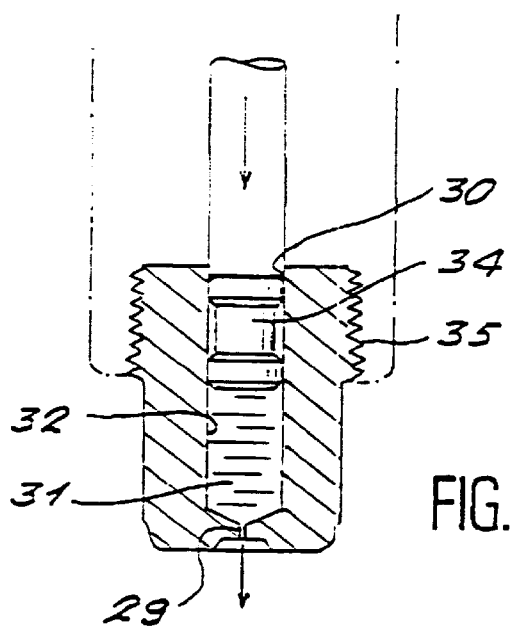
FIG. 5 is a sectional view illustrating the movement of the striker on the elastomeric stopper contained in the cartridge.

According to another embodiment FIGS. 3–5 of the cartridge 28, the cartridge is empty and is filled by the user just before use.

The outer envelope of the said cartridge moreover has, on the one hand, means of fixing 35, 35' to the said body (screw pitch, spike, etc.) and, on the other hand, raised zones 36 allowing it to be gripped by the user. The front face corresponding to the nozzle comprises, if appropriate, a basin 37 whose depth is variable but guarantees that the jet issuing from the orifice of the nozzle has the time needed to establish its hydrodynamics prior to the subcutaneous, intradermal or intramuscular injection.

The invention, as it has been described above, is very easy to use: there is no more sterilization, nor washing of the apparatus, while at the same time increased safety for the user is guaranteed because of the absence of a needle and the impossibility of reusing it without first having reloaded the apparatus with a new dose, the method of fixing the cartridge avoiding all the risks of the latter bursting because of the absence of a breech. This invention is advantageously adapted for use by a single user having no specific knowledge in the field of subcutaneous, intradermal or intramuscular injections, and it reduces, on the one hand, the risks of accidents, which are always possible with an injection means having a needle, and, on the other hand, it eliminates the fear of stick injuries and any risk of contamination. The use of this device also allows the patient's chronobiology to be taken into consideration. This invention will have advantageous developments in the injection of a dose of small volume, in particular of 0.05 to 0.2 ml. It is of special interest for the administration of medicaments or vaccines to man or animals. Among other products which may be mentioned are polypeptides or peptides, such as enzymes and particularly calcitonin, used for the prevention of loss of bone substance and the treatment of osteoporosis, or else medicaments against migraine. Other products, in particular polypeptides or peptides, which may be administered using the device forming the subject of the invention, include hormones, such as insulin, somatostatin, the growth hormone, clotting factors, for example antihaemophilic factors, plasma components, such as erythropoietin, antiviral polypeptides, such as interferons, or immunomodulators, such as lymphokines. This device is also especially appropriate for the administration of vaccine preparations.

Of course, the present invention is not limited to the illustrative embodiments which have been described and represented above, but can encompass all variants thereof.

Thus, the cartridges can be presented before the rod of the striker with the aid of a barrel or a charger, and they can also comprise the dose of the product to be injected.

What is claimed is:

1. In a needle-free single use injection device of a pharmaceutical product, the device having a cap relatively movable relative to a device body for triggering a percussion member contained in the body, a cartridge mounted to a delivery end of the device, the cartridge containing the product and driven by the percussion member, and the cartridge comprising:

a receptacle of preselected material and containing a single use quantity of the pharmaceutical product;

a single orifice formed in the receptacle for providing an exit for a jet of injected pharmaceutical product;

an envelope made of a preselected material and molded over the receptacle;

an end cap removably covering a delivery end of the cartridge that includes the single orifice;

an elastomeric seal located in a central portion of the end cap for sealing the orifice;

and further wherein the end cap has lateral walls which enclose the delivery end of the cartridge, the walls of the end cap being provided with raised zones allowing them to be clipped into impressions provided on the outer lateral walls of the cartridge, thus ensuring that the end cap is held on the cartridge.

2. In a needle-free single use injection device of a pharmaceutical product, the device having a cap relatively movable relative to a device body for triggering a percussion member contained in the body, a cartridge mounted to a delivery end of the device, the cartridge containing the product and driven by the percussion member, and the cartridge comprising:

a receptacle of preselected material and containing a single use quantity of the pharmaceutical product;

a single orifice formed in the receptacle for providing an exit for a jet of injected pharmaceutical product;

an envelope made of a preselected material and molded over the receptacle;

an end cap removably covering a delivery end of the cartridge that includes the single orifice;

an elastomeric seal located in a central portion of the end cap for sealing the orifice;

and further wherein an outer wall of the end cap forms a grip zone which allows a user to position studs of the cartridge in line with bayonets of the injection device.

3. In a needle-free single use injection device of a pharmaceutical product, the device having a cap relatively movable relative to a device body for triggering a percussion member contained in the body, a cartridge mounted to a delivery end of the device opposite the cap, the cartridge containing the product and driven by the percussion member, and the cartridge comprising:

a receptacle of preselected material and containing a single use quantity of the pharmaceutical product;

a single orifice formed in the receptacle for providing an exit for a jet of injected pharmaceutical product;

an envelope made of a preselected material and molded over the receptacle;

an end cap removably covering a delivery end of the cartridge that includes the single orifice;

an elastomeric seal located in a central portion of the end cap for sealing the orifice;

and further wherein the elastomeric seal is obtained during simultaneous moulding operation of the cap.

4. In a needle-free single use injection device of a pharmaceutical product, the device having a cap relatively movable relative to a device body for triggering a percussion member contained in the body, a cartridge mounted to a delivery end of the device opposite the cap, the cartridge containing the product and driven by the percussion member, and the cartridge comprising:

a receptacle of preselected material and containing a single use quantity of the pharmaceutical product;

a single orifice formed in the receptacle for providing an exit for a jet of injected pharmaceutical product;

an envelope made of a preselected material and molded over the receptacle;

an end cap removably covering a delivery end of the cartridge that includes the single orifice;

an elastomeric seal located in a central portion of the end cap for sealing the orifice;

and further wherein the elastomeric seal is attached and fitted by force into a recess provided in an internal surface of the end cap.

5. In a needle-free single use injection device of a pharmaceutical product, the device having a cap relatively movable relative to a device body for triggering a percussion member contained in the body, a cartridge mounted to a delivery end of the device opposite the cap, the cartridge containing the product and driven by the percussion member, and the cartridge comprising:

a receptacle of preselected material and containing a single use quantity of the pharmaceutical product;

a single orifice formed in the receptacle for providing an exit for a jet of injected pharmaceutical product;

an envelope made of a preselected material and molded over the receptacle;

an end cap removably covering a delivery end of the cartridge that includes the single orifice;

an elastomeric seal located in a central portion of the end cap for sealing the orifice; and a plurality of gaps, formed in the thickness of the envelope molded over the cartridge, in order to produce slots for improving the visibility of the receptacle.

* * * * *